(12) United States Patent
Frycek et al.

(10) Patent No.: US 9,809,529 B2
(45) Date of Patent: Nov. 7, 2017

(54) PROCESS FOR PRODUCING LOW VOC COALESCING AIDS

(71) Applicant: Dow Global Technologies LLC, Midland, MI (US)

(72) Inventors: George J. Frycek, Midland, MI (US); Felipe A. Donate, Midland, MI (US); Edward D. Daugs, Midland, MI (US); Rebecca J. Wachowicz, Bay City, MI (US); Jason L. Trumble, Bay City, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/318,032

(22) PCT Filed: Jun. 18, 2015

(86) PCT No.: PCT/US2015/036387
§ 371 (c)(1),
(2) Date: Dec. 12, 2016

(87) PCT Pub. No.: WO2015/200087
PCT Pub. Date: Dec. 30, 2015

(65) Prior Publication Data
US 2017/0129843 A1    May 11, 2017

Related U.S. Application Data

(60) Provisional application No. 62/016,301, filed on Jun. 24, 2014.

(51) Int. Cl.
| C07C 69/76 | (2006.01) |
| C07C 67/08 | (2006.01) |
| C07C 67/54 | (2006.01) |

(52) U.S. Cl.
CPC .............. C07C 67/08 (2013.01); C07C 67/54 (2013.01)

(58) Field of Classification Search
CPC .......... C07C 67/08; C07C 67/54; C07C 69/78
See application file for complete search history.

(56) References Cited

U.S. PATENT DOCUMENTS

| 4,022,808 | A | 5/1977 | Yoshihara et al. |
| 4,115,415 | A | 9/1978 | Yoshihara et al. |
| 4,489,188 | A | 12/1984 | Jones et al. |
| 5,618,973 | A | 4/1997 | Papa et al. |
| 6,916,950 | B2 | 7/2005 | Gubisch et al. |
| 2012/0258249 | A1 | 10/2012 | Adamson et al. |
| 2012/0259049 | A1 | 10/2012 | Donate et al. |

FOREIGN PATENT DOCUMENTS

| CA | 2746599 A1 | 7/2010 |
| WO | 2014/052298 A2 | 4/2014 |

OTHER PUBLICATIONS

Ishihara, "Dehydrative condensation catalyses", Tetrahedron 65, 2009, pp. 1085-1109.
Brewster, et al, "Unitized Experiments in Organic Chemistry", 3rd Edition, 1970, pp. 101-105.
"Acetyl Chloride Method", Organic Syntheses, Collective vol. 3, 1955, p. 142-144.
PCT/US2015/036387, International Search Report and Written Opinion dated Sep. 21, 2015.
PCT/US2015/036387, International Preliminary Report on Patentability dated Jan. 5, 2017.

*Primary Examiner* — Jafar Parsa
*Assistant Examiner* — Blaine G Doletski

(57) ABSTRACT

A process comprising reacting a benzoic acid with a glycol ether in the presence of phosphoric acid to produce a glycol ether ester product having low color, low odor, and low VOC content.

13 Claims, No Drawings

PROCESS FOR PRODUCING LOW VOC COALESCING AIDS

BACKGROUND OF THE INVENTION

The invention relates to a process for the preparation of low volatile organic compound (VOC) glycol ether esters.

Coalescing aids are added to waterborne paints (i.e., latex paints) to allow the formation of a continuous polymer or binder film as water evaporates from the system. Without the addition of these coalescing aids, latex polymer spheres are not likely to soften and deform, which is a requirement for film formation. As a result, the polymer cannot act as a binder for the pigments in the paint and no adhesion to the substrate (e.g., interior or exterior wall) can occur. For many years, coalescing aids have been volatile solvents, such as 2,2,4-trimethyl-1,3-pentanediol monoisobutyrate, commercially available from Eastman under the trade name TEXANOL. Color, odor and the VOC status are increasingly important properties of solvents used as coalescing aids for paints.

In the United States of America, VOC regulations established by the Environmental Protection Agency (EPA) and enforced at the state level dictate the maximum concentration of volatile solvents in paints and other products. In Europe, VOC limits are defined by the 2004/42/EC Solvents Directive for Decorative Paints, under which a substance having a boiling point below 250° C. at 760 mmHg is considered a VOC. France has a more stringent regulation. French Law decree 321/2011, part of the "Grenelle de l'environnement" initiative, defines a substance with a boiling point below 280° C. as a VOC. Water is a volatile component of waterborne paints but it is exempt from VOC regulations as it does not contribute to smog generation. VOC regulations have become more and more stringent to the point that coalescing aids with zero or very low VOC content are now required in order to meet them.

US 2012/0258249 and US 2012/0259049 teach the use of various glycol ether esters as zero VOC coalescing aids and clean-up solvents, respectively. Several preparation methods are described in these patent applications. One of these methods is the Fischer esterification reaction, in which a stoichiometric excess of a reactant bearing a hydroxyl group (e.g., an alcohol or glycol ether) and a carboxylic acid are heated in the presence of a catalytic amount of a strong acid (e.g., concentrated sulfuric acid) and an entrainer solvent (i.e., heptane, toluene, etc.) to yield the desired ester. By-product water is removed by azeotropic distillation. An example of this synthesis can be found in "Unitized Experiments in Organic Chemistry" $3^{rd}$ Edition, by Brewster, VanderWerf, and McEwen, pp. 101-105 (1970). Another method of preparation employs the acid chloride (or dichloride) instead of the carboxylic acid as a reactant. In this case, hydrogen chloride gas is given off instead of water during the reaction. The hydrogen chloride is trapped by the addition of a tertiary amine to the reaction mixture or by means of a water scrubber ("Organic Syntheses, Collective Volume 3," p. 142 (1955)). Another method of preparation, as disclosed in RD 1987276098 A, involves the transesterification of an alkyl ester of the desired acid with a glycol ether in the presence of a suitable catalyst such as tetraisopropyl titanate. Still another method of esterification uses the acid anhydride as reactant in combination with the azeotropic removal of water in the presence of an entrainer. This latter method is often aimed at producing diesters; see, e.g., CA 2,356,469.

Additional processes for the preparation of glycol ether esters are described in the literature. EP 0711747 B1 teaches that sulfuric acid and p-toluene sulfonic acid catalysts produce color issues in the synthesis of glycol ether acetates by direct esterification, i.e., the Fischer reaction. Products are recovered and purified by distillation. CA 2,746,599 discloses a direct esterification process using as reactants carboxylic and dicarboxylic acids, $C_4$-$C_{13}$ alcohols, alkylene glycol monoethers, and polyalkylene glycol monoethers in the presence of a Lewis acid or Bronsted acid catalyst over a broad reaction temperature range (160-270° C.), and requires a minimum alcohol concentration of a 30% excess of the stoichiometric amount. That patent teaches that higher temperatures increase the formation of colored by-products.

Aranda et al., in *Catal. Lett.* (2008) 122:20-25, reported the use of various acids as transesterification catalysts for fatty acids, such as palm oil, for the production of biodiesel. Methanesulfonic and sulfuric acid were the best catalysts, while trichloroacetic acid and phosphoric acid performed poorly.

In addition to low or zero VOC, low odor is also a highly desirable property for a coalescing aid. Paints made using a coalescing aid with a strong odor can have limited acceptance by consumers in spite of other positive attributes. Paints with a strong odor may require well-ventilated areas for their application, which may limit their use indoors, especially by the non-professional user. If an aldehyde such as butanal is present as an impurity in a coalescent, the resulting paint can acquire a strong and obnoxious odor, as butanal has a characteristically pungent and disagreeably sweet aldehyde odor. Butanal can also oxidize into butyric acid, the carboxylic acid found in rancid butter and vomit.

The aforementioned processes often yield reaction mixtures that have undesirable odors and color. Color often arises from decomposition of one of the reactants. A cumbersome, expensive activated charcoal treatment can be used to improve the color and odor of a relatively non-volatile product.

It would be desirable to have an improved process for the preparation of low-VOC glycol ether esters that would allow production of the desired products in high yield without the need for further treatment, such as charcoal treatment, to remove color and undesirable odor.

SUMMARY OF THE INVENTION

The process of the invention is such a process for the preparation of a glycol ether ester, the process comprising contacting in a reaction zone benzoic acid and/or benzoic acid anhydride with a glycol ether feed and a catalytic amount of phosphoric acid to form a reaction mixture under reaction conditions sufficient to produce a glycol ether ester product and water, wherein the feed comprises a glycol ether and butanal, and wherein the water and butanal are at least partially vaporized in the reaction zone and are passed to a separation zone where the water and butanal are substantially removed from the separation zone, thus providing a first crude product comprising the glycol ether ester, and wherein the process is operated under conditions of temperature and pressure such that substantially no glycol ether leaves the separation zone, other than as a component of an azeotrope.

Surprisingly, the process employs phosphoric acid as a catalyst to prepare glycol ether ester solvents with low, or near zero, VOC content as determined by French Law decree 321/2011, and can produce said solvents with low color levels and low levels of odor-inducing butanal.

DETAILED DESCRIPTION OF THE INVENTION

The process of the invention employs benzoic acid and/or anhydride, a glycol ether, and a phosphoric acid catalyst. The catalyst and the sequence of process steps provide a means to obtain odorless, butanal-free, low color glycol ether ester products with good yield.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

For the purposes of the invention, the term "low boiling" refers to materials having boiling points lower than the boiling point of the relevant glycol ether ester.

For the purposes of the invention, the term "odorless" refers to materials having a butanal content of less than 5 ppm as measured by gas chromatography.

For the purposes of the invention, the term "reaction system" refers to a reactor or a plurality of reactors. A plurality of reactors, if employed, is preferably connected in series.

The benzoic acid contains carboxyl groups that may, alternatively, be present in the form of anhydride groups. Mixtures of benzoic acid and anhydrides can be employed. Benzoic acid is preferred. In one embodiment of the invention, benzoic acid is employed as the carboxylic acid in the substantial absence of anhydrides.

The glycol ether employed is represented by Formula I:

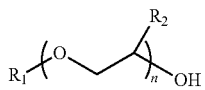

where $R_1$ is a $C_1$-$C_{10}$ alkyl group, phenyl, or benzyl, $R_2$ is H, methyl or ethyl, and n is 1 to 3. In one embodiment of the invention, $R_1$ is a $C_1$-$C_4$ alkyl group. Examples of suitable glycol ethers include ethylene glycol n-butyl ether, ethylene glycol n-hexyl ether, diethylene glycol phenyl ether, tripropylene glycol methyl ether, dipropylene glycol phenyl ether, tripropylene glycol n-butyl ether, dipropylene glycol n-butyl ether, dipropylene glycol n-propyl ether, diethylene glycol n-butyl ether, diethylene glycol n-hexyl ether, butylene glycol ethyl ether, butylene glycol propyl ether, butylene glycol hexyl ether, and dibutylene glycol methyl ether. Mixtures of glycol ethers may be employed. In one embodiment of the invention, the molar ratio of glycol ether to carbonyl moiety of benzoic acid or anhydride is from 1.10 to 1.6, i.e., from 1.10 to 1.6 moles of glycol ether are employed per mole of carbonyl moiety. In other embodiments, this ratio is from 1.15 to 1.4, or 1.2 to 1.3. In one embodiment of the invention, the glycol ether fed to the process contains butanal. For example, the butanal content of the glycol ether feed stream can be from 15 to 1,200 ppm or more, or can be from 50 to 1,000 ppm or more.

Phosphoric acid is widely commercially available. The phosphoric acid is employed in a catalytic amount. Advantageously, the amount of phosphoric acid is from about 1.0 to about 3.5, preferably from 1.5 to 2.5, mole percent, more preferably 1.9 to 2.1, based on the total moles of benzoic acid and anhydride. In one embodiment of the invention, the phosphoric acid is employed in the form of an aqueous solution. The phosphoric acid content of the solution is not particularly critical, although increased corrosion may be observed with higher concentrations, depending on the materials of construction employed. In one embodiment of the invention, the phosphoric acid is supplied as an aqueous solution of 85% phosphoric acid.

The process is an esterification process that operates under a set of reaction and process conditions that allow the glycol ether ester products to be produced in a relatively short reaction time in a direct esterification process (i.e., Fischer reaction), in high yield, and relatively free of color and undesirable odors.

In one embodiment, the invention is a process for preparing benzoic esters by reacting a benzoic acid or a benzoic anhydride or a mixture thereof with a glycol ether in a reaction system comprising at least one reactor, with water being distilled off in a separation zone as a glycol ether-water azeotrope with the vapor coming out of the reaction liquid, the vapor then being at least partly condensed, and at least part of the condensate being returned as reflux to the separation zone. In one embodiment of the invention, the separation zone comprises a distillation column and the distillation column is operated using a process control scheme that includes controlling the temperature at the top of the column.

In one embodiment of the invention, the process is conducted in a reactor equipped with a distillation column. The column may be separate from the reactor or, preferably, is a column mounted on the reactor. The column advantageously is equipped with or connected to a condenser. As the reaction proceeds, by-product water of reaction forms an azeotrope with the glycol ether. The reactor and column advantageously are operated under conditions of temperature, pressure and reflux ratio such that essentially only the azeotrope exits the column overhead. In this manner, essentially no glycol ether reactant leaves the column, other than as a component of the azeotrope. Water vapor is removed from the reactor as a component of the azeotrope. The vapor is condensed, and part of the condensate is returned as reflux to the column. The amount of condensate returned is determined by the temperature of the condensate and by the energy balance requirements of the system. In one embodiment of the invention, the operation of the column is controlled by observing the temperature at the top of the column. The temperature can also be observed at other points in the column, as is known to those skilled in the art. In one embodiment of the invention, the process is conducted in the substantial absence of oxygen.

In one embodiment of the invention, the temperature and pressure conditions are such that the temperature of the reaction mixture is lower than its boiling point. The process advantageously employs a reaction temperature of from 170 to 210° C., i.e., the average temperature of the liquid in the reaction zone advantageously is in this range. The reaction pressure is, as is known to those skilled in the art, related to the reaction temperature and the extent of completion of the reaction. In various embodiments of the invention, the reaction pressure can be from 10 to 2500 mmHg absolute (1.3 kPa to 333 kPa), or from 50 mmHg (6.7 kPa) to 760 mmHg absolute (101 kPa).

In one embodiment of the invention, as the reaction proceeds, by-product water is removed via the column, and the desired product concentrates in the reactor. The extent of completion of the reaction can be observed by tracking the amount of water produced, or by other methods known to those skilled in the art. For the purposes of the invention, the term "first crude product" refers to the liquid contents of the reactor at the completion of the reaction of the glycol ether with the benzoic acid.

The starting materials and the catalyst can be introduced into the reactor in any suitable order, e.g., either simultaneously or otherwise, when the process is carried out batchwise. The catalyst can be introduced in pure form or as a solution, preferably as a solution in water or one of the starting materials, at any suitable point in the process.

In the case of a continuous process, streams of the starting materials and of the catalyst are fed into the reactor or, when a reactor cascade is used, preferably into the first reactor of the cascade. The residence time in the reactor or the individual reactors is determined by the volume of the reactors and the flow rate of the starting materials. Benzoic acid is normally a solid at room temperature. Accordingly, for a continuous process it may be desirable to feed it as a solution where the solvent is, for example, the glycol ether reactant.

The reaction can be conducted in any suitable equipment, using any suitable materials of construction, as is well known to those skilled in the art.

In one embodiment of the invention, at the end of the reaction, an alkaline material is contacted with the first crude product under conditions sufficient to neutralize the major portion of any acids therein, thereby forming a neutralized crude product mixture comprising a glycol ether ester product and at least one salt. For example, the catalyst and residual benzoic acid can be neutralized using the alkaline material. In one embodiment of the invention, all of the catalyst is neutralized, i.e., at least the first hydrogen atom of the phosphoric acid catalyst is replaced with some portion of a molecule of the alkaline material, and at least a portion of any residual unreacted benzoic acid is neutralized. In one embodiment of the invention, at the end of the reaction, the first crude product is at least partially cooled prior to and/or during neutralization.

The alkaline material advantageously is employed in an amount that is sufficient to neutralize the major portion of any acids therein, thereby forming a neutralized crude product mixture. The amount of alkaline material required can readily be determined by those skilled in the art. Examples of alkaline materials include: glycol ether alkoxides; alkali metal and alkaline earth metal compounds, such as NaOH, MgOH, CaOH, KOH, sodium carbonate and sodium bicarbonate; alkaline solids, such as alkaline alumina and alkaline ion exchange resins; and the like. Sodium carbonate is preferred. Soluble alkaline materials preferably are added as a solution using an appropriate solvent, e.g., water or a glycol ether. Mixtures of alkaline materials can be employed.

In one embodiment of the invention, the process further comprises extracting one or more salts formed during neutralization. This advantageously is accomplished by allowing the salts to migrate to the aqueous phase of a multiphase mixture that forms when the alkaline material is introduced to the first crude product. The extraction step is conducted for the purpose of separating the salts, which are produced by the neutralization step, from the neutralized crude product mixture. The extraction step may aid in color and odor removal from the product. The extraction optionally can involve adding additional solvent, e.g., water, and/or an extraction aid, to the first crude product and/or the neutralized crude product mixture to facilitate extraction of the salts.

The optional extraction aid is a water-soluble material that serves at least one of the following functions: to break potential emulsions; to improve the separation of the aqueous and organic layers; and/or to improve the extraction of the salts into the aqueous phase. The amount of extraction aid that may be employed can readily be determined by those skilled in the art. In one embodiment of the invention, from 0.1 to 10 weight parts of extraction aid are employed per 100 weight parts of the neutralized crude product mixture. Examples of suitable extraction aids include water-miscible organic species such as ketones, such as acetone, and alkanols, such as isopropanol and n-propanol. Mixtures of extraction aids can be employed.

The neutralization and extraction may be performed concurrently or sequentially. If performed sequentially by first conducting the neutralization, and then conducting the extraction, as will be recognized by those skilled in the art, it is likely that some extraction will occur during the neutralization. Thus, regardless of whether an extraction aid is added toward the start of neutralization of after neutralization is complete, neutralization and extraction are occurring simultaneously, to some extent. For the purposes of the invention, the term "simultaneously," when used in connection with the neutralization reaction and extraction of the reaction product, means that at some point the extraction and the neutralization reaction are both occurring at the same time. As will be recognized by those skilled in the art, at the start of the neutralization reaction there will be very little to no extraction occurring. The rate of extraction will increase as more salt becomes available in the neutralized crude product mixture. Thus, as a practical matter, once a salt forms as a result of neutralization, it is possible for some extraction to occur, as is well known to those skilled in the art.

In various embodiments of the invention, the process comprises adding water, and optionally an extraction aid, to the first crude product and/or the neutralized crude product mixture to extract the salt(s) formed during neutralization, and allowing phase separation, then recovering the organic phase comprising the product. Recovery of the organic phase can be accomplished by separating either the organic phase or the aqueous phase from the other phase. For example, the organic phase can be decanted from the aqueous phase to obtain a salt-free crude product. The organic phase is retained for further processing. The salt-containing aqueous phase can be discarded or can be processed to recover its contents according to methods well known to those skilled in the art.

Following the recovery of the organic phase, which for the purposes of the invention is also referred to as a "salt-free crude product," the salt-free crude product is purified, i.e. processed to recover the final product using methods known to those skilled in the art. For example, water, glycol ether, and low boiling organics, such as butanal, can be removed from the salt-free crude product by any suitable means including, for example, distillation, vacuum stripping with an inert gas, such as nitrogen, or a combination thereof to produce a final glycol ether ester product as an overhead product. Advantageously, the maximum stripping temperature is below 170° C. in order to minimize the formation of color and odor bodies. In one embodiment of the invention, the salt-free crude product is vacuum stripped then distilled. The conditions employed can be readily determined by those skilled in the art, depending on the product being produced.

An optional filtering step may be employed as needed to remove solid salts from the liquid phase. This filtering step can be performed as desired at various points in the process, as is known to those skilled in the art. In one embodiment of the invention, the process is conducted without a filtering step.

In a particularly preferred embodiment of the invention, the process is a process for the production of ethylene glycol n-butyl ether benzoate. This embodiment includes following steps:

(1) Reacting ethylene glycol n-butyl ether and benzoic acid in the presence of a catalytic amount of phosphoric acid, with removal of by-product water by azeotropic distillation to form a first crude product. In order to minimize the loss of reactants during the reaction step, the temperature and pressure conditions in the system are such that the temperature of the reaction mixture is lower than its boiling point.

(2) Cooling the first crude product to 80° C. or lower.

(3) Neutralizing the phosphoric acid catalyst, and at least some benzoic acid, by adding aqueous sodium carbonate to produce a neutralized crude product mixture.

(4) Extracting the salts, such as sodium phosphate, and salts of organic by-products, from the neutralized crude product mixture followed by phase separation and decanting to recover the organic phase.

(5) Purifying the organic phase. This involves removing residual water, ethylene glycol n-butyl ether and lighter, i.e., lower boiling point, organics, such as butanal, under vacuum using heating, with inert gas stripping, e.g., with nitrogen. The resulting material in the reaction vessel is then distilled at a lower pressure to obtain a final product overhead.

Thus, in one embodiment of the invention, the process is a process for the production of ethylene glycol n-butyl ether benzoate, the process comprising:

(1) admixing ethylene glycol n-butyl ether, benzoic acid, and a catalytic amount of phosphoric acid to form a reaction mixture, and reacting the ethylene glycol n-butyl ether with the benzoic acid with removal of by-product water by azeotropic distillation to form a first crude product, with the proviso that the temperature of the reaction mixture is lower than its boiling point;

(2) cooling the first crude product to 80° C. or lower;

(3) neutralizing the phosphoric acid catalyst, and at least some benzoic acid, by adding aqueous sodium carbonate to produce a neutralized crude product mixture that comprises salts;

(4) extracting the salts, such as sodium phosphate, and salts of organic by-products, from the neutralized crude product mixture followed by phase separation and decanting to recover the organic phase; and (5) purifying the organic phase by removing residual water, ethylene glycol n-butyl ether and lighter, i.e., butanal and other lower boiling point, organics, under vacuum using heating, with inert gas stripping, e.g., with nitrogen. The resulting material in the reaction vessel can then be distilled at a lower pressure to obtain a final product overhead.

The catalyst, and various aspects of the specific conditions and step sequence are important to obtain low color, odorless material with good yield from the feed material. For example, deviation from the temperature/pressure condition mentioned in step (1) leads to higher potential for the formation of undesirable impurities in the product. Doing step (5) before the neutralization may also lead to impurities formation in the material. In the absence of the extraction step (4), the final product may contain additional intermediate by-products, particularly, residual salts, benzoic acid and oxidation products of butanal.

The glycol ether ester product of the process is described by Formula II:

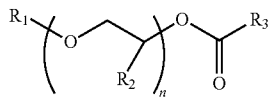

where $R_1$ is a $C_1$-$C_{10}$ alkyl group, phenyl or benzyl, $R_2$ is either hydrogen, methyl or ethyl, $R_3$ is phenyl, and n=1 to 3. Some examples of glycol ether esters described by this formula include ethylene glycol n-butyl ether benzoate, diethylene glycol phenyl ether benzoate, tripropylene glycol methyl ether benzoate and tripropylene glycol n-butyl ether benzoate.

In one embodiment of the invention, the final product contains less than 1% of volatile organic compounds as defined by French Law decree 321/2011. In one embodiment of the invention, the color of the product is less than 25 APHA, as measured by ASTM D1209.

SPECIFIC EMBODIMENTS OF THE INVENTION

The following example is given to illustrate the invention and should not be construed as limiting its scope. All pressures are absolute, not gauge, unless otherwise indicated.

Example 1: Manufacture of Ethylene Glycol N-Butyl Ether Benzoate (BUCSB)

A 10-gallon, 316 stainless steel reactor, rated for 750 psig (5.27 Mpa), equipped with a variable speed agitator/impeller, a nitrogen sparger, a cartridge filter, and a multiple use pipeline header is used. The reactor body is jacketed and the reactor head is traced to provide means for heating and cooling with SYLTHERM 800 brand heat transfer fluid, which is available from The Dow Chemical Company. The reactor is connected to a 5-foot×4-inch stainless steel, jacketed column packed with 5 feet of Goodloe brand structured packing. The column is equipped with an overhead 316 stainless steel, 2-pass heat exchanger with a total surface area of 25 square feet as a condenser, which is connected to a receiving vessel and to a vacuum system. The head of the reactor is operated at reduced temperature relative to the reactor jacket to minimize degradation reactions. For the reaction, the reactor head tracing and the column jacket are operated at the same temperature of 95° C. This is selected to minimize the loss of reactants in the overheads. The reactor and peripheral equipment are operated with a process control unit.

The following materials are charged to the reactor, in kg: 12.5 benzoic acid, 15.2 Butyl CELLOSOLVE brand ethylene glycol n-butyl ether (available from The Dow Chemical Company), 0.2 85% phosphoric acid (aq.). The mixture contains a 1.25 molar ratio of Butyl CELLOSOLVE (BUCS) to benzoic acid and 2 mol % of phosphoric acid based upon benzoic acid.

The reaction and simultaneous distillation steps are performed as follows: The initial materials are well mixed at 120 rpm using the built in agitator/impeller. The initial butanal, contributed by the BUCS, concentration in the reaction mixture is about 310 ppm. The initial pressure in the reactor is 40 psia (377 kPa), which is ramped down to 625 mmHg (83.3 kPa) at a rate designed to stay above the reaction mixture bubble point. The reactor is heated up to 210° C., and is maintained at that temperature for ca. 6 hours to allow the reaction to proceed. The pressure is then reduced to 500 mmHg (66.7 kPa), which is below the bubble point, to clear the column of azeotrope vapor. Reflux is applied to the column to let the BUCS-water azeotrope pass to the condenser and minimize excess BUCS from distilling out. Nitrogen stripping is conducted while the reaction proceeds in order to assist removal of butanal from the reactor.

The progress and rate of the esterification reaction between BUCS and benzoic acid are monitored by the recovered distillate, the rate of column overhead distillate, and by gas chromatography (GC) analysis of samples from the overheads and reactor. At the end of the reaction step, when the recovered overhead distillate mass approaches the expected target, the distillate flow rate approaches zero, and the GC analyses show most of the benzoic acid is converted, the reactor is pressurized to 760 mmHg (101.3 kPa) with nitrogen and cooled to 80° C. The reactor contents are analyzed by GC. No butanal is detected; the butanal detection limit is ≤0.3 ppm. The reactor contents contain 2.59 wt % benzoic acid. 8.54 wt % BUCS, and 85.94 wt % BUCSB as determined by GC, with an analytical precision of +/−5%.

The GC analysis is performed using a Hewlett-Packard 6890 Gas Chromatograph equipped with flame ionization (FID) and thermal conductivity (TCD) detectors, and a Hewlett-Packard 7673 auto-injector with a 100-sample tray. The instrument is linked to a Hewlett-Packard ChemStation comprising an IBM computer with HP62070AA software. The reaction components are analyzed on a 15 m×0.32 mm ID×1.0μ film phenomenex ZB-5 capillary column using a constant helium column pressure of 7 psig (149.6 kPa).

The weight amount of sodium carbonate required for neutralization is calculated, and that amount is added to the reactor as a 10 weight % aqueous solution. The amount of sodium carbonate for the neutralization is determined using the formula:

$$Na_2CO_3(kg)=(2.35\times moles\ H_3PO_4)+(residual\ moles\ benzoic\ acid)$$

The addition of the solution triggers phase separation. The aqueous phase makes up about 25% of the liquid in the reactor. The reactor contents are stirred for 1 hour before decanting the bottom (aqueous) layer.

The final distillation step is done in 2 parts. In the first part, the reactor is heated to 145° C. and the pressure set at ca. 225 mmHg (30 kPa) with full take-off and nitrogen sparge to remove water and unreacted BUCS. The temperature is later raised to 150° C. and the reactor pressure is set at 10 mmHg (1.33 kPa) with a slight nitrogen sparge to remove the remainder of the BUCS. The product ethylene glycol n-butyl ether benzoate (BUCSB) is then cooled and drained from the reactor through a cartridge filter into a storage vessel.

For the $2^{nd}$ part of the final distillation, product from 2 runs of the preceding procedure are combined (a total of 23.65 kg) and are loaded into the reactor with nitrogen pressure. The column pressure is reduced to 5 mmHg (0.667 kPa), the reactor pressure to ca. 30 mmHg, and the reactor heat transfer fluid temperature is set to 210° C. The resulting temperature of the reaction mixture (bottoms) is ca. 180-185° C. An overhead temperature of 145-150° C. at ca. 5 mmHg (0.667) is observed, which is consistent with the ethylene glycol n-butyl ether benzoate boiling point. The butanal content of the final BUCSB product is below the GC detection limit of 0.3 ppm. The distilled overhead product contains 100.5 wt % BUCSB as determined by GC. The BUCSB product is visually colorless (APHA color of 5.9), meets the zero VOC criteria for the French law Decree 3231/2011, and is odorless.

Comparative Experiment 2 Manufacture of BUCSB with Sulfuric Acid Catalyst (not an Embodiment of the Invention)

A 22 liter glass reactor is used. The reactor is equipped with a thermocouple well, a large magnetic Teflon stirring bar, and a heating mantle connected to a temperature controller fitted with control and high limit thermocouples. The heating mantle has a built-in magnetic stirrer. The reactor has several tapered female glass joints of various sizes that are capped with glass stoppers if not required for the reaction. Attached to a center 55/50 joint is an Airfree® Solvent Distillation Apparatus from Chemglass® (# AF-0720) that is modified with a 1-inch vapor tube to facilitate solvent flow back into the reactor. This unit has a built-in condenser and performs as a Dean-Stark trap to separate water from the azeotroping solvent. A dropping funnel with a pressure-equalizing arm containing a known weight of heptane is attached to the top of the Airfree unit. A nitrogen adapter, which is teed-off to a bubbler and which is connected with Tygon® tubing to a 2 psig (115.1 kPa) nitrogen line, is placed on top of the dropping funnel. The entire apparatus is clamped securely to the lattice of a large fume hood and is placed inside large trays serving as secondary containers.

The following materials are charged to the reactor, in kg: 8.22 benzoic acid, 8.36 BUCS, 0.07 concentrated sulfuric acid, and 1.88 heptane. The molar ratio in the reaction mixture of BUCS to benzoic acid is 1.1:1 and the mixture contains 1.1 mole % sulfuric acid based upon benzoic acid. The initial butanal, contributed by the BUCS, concentration in the reaction mixture is about 310 ppm.

The benzoic acid, BUCS, sulfuric acid, and 0.89 kg heptane are loaded into the reactor. The reaction mixture is stirred and heated gradually to establish a constant heptane reflux through the trap where the water of esterification is collected. Water and heptane begin to distill over at about 99-103° C. and a pot temperature of about 130° C. As water is removed, the rest of the heptane (0.99 kg) is added to the reaction mixture from the funnel to keep the reaction mixture refluxing at a maximum temperature of 150° C. The reaction is continued until the total amount of water removed indicates that the reaction is essentially complete (15 hours). The water phase amounts to 1.3 kg which includes some BUCS that codistills as part of a water-BUCS azeotrope. A total of 0.5 kg heptane is recovered from the trap.

The reactor is cooled and the reaction mixture is titrated for total acidity. A 30 wt % excess of 20% aqueous NaOH is added to the mixture to neutralize all acid equivalents of the sulfuric acid and some of the residual benzoic acid. The reaction mixture is stirred for about 1 hour before verifying the neutralization of the sulfuric acid with another sample titration. The brownish-yellow neutralized crude product mixture is then pumped out of the reactor into a tared 55-gallon polyethylene drum. The foregoing procedure is repeated, and the drum is used to collect the neutralized mixture of several batches.

A total of 31.38 kg of neutralized crude product mixture is loaded from the drum into the 10 gallon reactor of Example 1. The mixture is neutralized and extracted with 10% sodium carbonate as described in Example 1 in order to neutralize all residual acid. After stirring for one hour, the bottom layer is decanted.

The reactor is heated to 170° C. at a reactor pressure of ca. 50 mmHg (6.67 kPa) with full take-off and a nitrogen sparge to remove water, heptane, and BUCS. The initial butanal content is about 2 ppm. After removing these light components, the overhead column pressure is reduced to 5 mmHg (0.667 kPa) and the reactor pressure to ca. 30 mmHg (4.0 kPa). The resulting temperature of the reactor contents (bottoms) is ca. 180-185° C. An overhead temperature of 145-150° C. at ca. 5 mmHg (0.667 kPa) is observed, which is consistent with the BUCSB boiling point. No nitrogen sparge is used. The butanal content of the distilled product, measured as the distillation progresses, is 17.2 ppm at the start and 54.9 ppm at the end, which shows that butanal cannot be removed from the product with the same distillation conditions used for the BUCSB produced with phosphoric acid, and in fact butanal appears to be forming during the distillation. The APHA color of the final product is 5.9. The BUCSB product meets the zero VOC criteria for the French law Decree 3231/2011, but has an undesirable odor, thereby making it unsuitable for use in paints.

These experiments illustrate the importance of the phosphoric acid catalyst. Butanal-free, odorless BUCSB is not obtained, even in distilled product, when the catalyst is sulfuric acid.

What is claimed is:

1. A process for the preparation of a glycol ether ester, the process comprising (a) contacting in a reaction zone benzoic acid and/or benzoic acid anhydride with a glycol ether feed and a catalytic amount of phosphoric acid, to form a reaction mixture, under reaction conditions sufficient to produce a glycol ether ester product and water, wherein the feed comprises a glycol ether and butanal, and wherein the water and butanal are at least partially vaporized in the reaction zone and are passed to a separation zone providing a first crude product and having a butanal content of less than 5 ppm, and wherein the process is operated under conditions of temperature and pressure wherein the maximum temperature in the separation zone in step (a) is less than the boiling point of the reaction mixture.

2. The process of claim 1 further comprising (b) contacting the first crude product with an alkaline material to produce a neutralized crude product mixture comprising an organic phase and an aqueous phase, the neutralized crude product mixture comprising a glycol ether ester product and at least one salt, and wherein the contacting is conducted under conditions sufficient to extract the at least one salt into the aqueous phase.

3. The process of claim 2 further comprising (c) allowing the neutralized crude product mixture to phase separate into a salt-containing aqueous phase and an organic phase, and recovering the organic phase.

4. The process of claim 3 further comprising (d) purifying the organic phase by removing residual water, glycol ether and lighter, i.e., lower boiling point, organics under vacuum using heating, optionally with inert gas stripping, to obtain a final glycol ether ester product as an overhead product.

5. The process of claim 1 wherein the temperature at the top of the separation zone in step (a) is at least the boiling point of the azeotrope.

6. The process of claim 1 wherein the azeotrope is formed by water and the glycol ether.

7. The process of claim 2 further comprising adding water, and optionally an extraction aid, in step (b) to the first crude product.

8. The process of claim 3 wherein, in step (c), recovering the organic phase comprises decanting to remove the salt-containing aqueous phase.

9. The process of claim 1 wherein the glycol ether ester product has an APHA a color of less than 25.

10. The process of claim 1 wherein the separation zone comprises a distillation column, wherein the temperature at the top of the column is controlled.

11. The process of claim 1 wherein the glycol ether feed has a butanal content of from 15 to 1,000 ppm.

12. The process of claim 1 wherein the glycol ether feed comprises a glycol ether of Formula I:

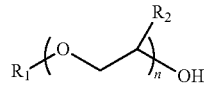

where $R_1$ is a $C_1$-$C_{10}$ alkyl group, phenyl, or benzyl, $R_2$ is H, methyl or ethyl, and n is 1 to 3.

13. The process of claim 1 wherein the glycol ether of the feed is ethylene glycol n-butyl ether and the ester is ethylene glycol n-butyl ether benzoate.

* * * * *